United States Patent
Kumta et al.

(10) Patent No.: US 11,590,266 B2
(45) Date of Patent: Feb. 28, 2023

(54) BIODEGRADABLE IRON-CONTAINING COMPOSITIONS, METHODS OF PREPARING AND APPLICATIONS THEREFOR

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Sung Jae Chung, Pittsburgh, PA (US); Partha Saha, Pittsburgh, PA (US); Oleg Velikokhatnyi, Pittsburgh, PA (US); Moni Kanchan Datta, Pittsburgh, PA (US); Dae Ho Hong, Pittsburgh, PA (US); Da-Tren Chou, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 278 days.

(21) Appl. No.: 16/559,810

(22) Filed: Sep. 4, 2019

(65) Prior Publication Data

US 2020/0000973 A1 Jan. 2, 2020

Related U.S. Application Data

(62) Division of application No. 14/045,011, filed on Oct. 3, 2013.

(60) Provisional application No. 61/710,338, filed on Oct. 5, 2012.

(51) Int. Cl.
| | |
|---|---|
| *C22C 38/00* | (2006.01) |
| *A61L 31/02* | (2006.01) |
| *A61L 31/14* | (2006.01) |
| *C22C 33/10* | (2006.01) |
| *C22C 38/14* | (2006.01) |
| *C22C 45/02* | (2006.01) |

(52) U.S. Cl.
CPC ......... *A61L 31/022* (2013.01); *A61L 31/148* (2013.01); *C22C 33/10* (2013.01); *C22C 38/00* (2013.01); *C22C 38/002* (2013.01); *C22C 38/14* (2013.01); *C22C 45/02* (2013.01)

(58) Field of Classification Search
CPC ....................................... C22C 38/00
See application file for complete search history.

(56) References Cited

U.S. PATENT DOCUMENTS

| | | |
|---|---|---|
| 2008/0082162 A1 | 4/2008 | Boismier et al. |
| 2008/0249637 A1 | 10/2008 | Asgari |
| 2011/0319977 A1 | 12/2011 | Pandelidis et al. |
| 2013/0243699 A1 | 9/2013 | Wang et al. |

FOREIGN PATENT DOCUMENTS

RU 2356984 C1 * 5/2009

OTHER PUBLICATIONS

English machine translation of RU 2356984 C1 of Shchepochkina published May 27, 2009 (Year: 2009).*
Wang, P., Zhao, J., Du, Y., Xu, H., Gang, T., Fen, J., Zhang, L., He, C., Liu, S. and Ouyang, H., 2011. Experimental investigation and thermodynamic calculation of the Fe—Mg—Mn and Fe—Mg—Ni systems. International Journal of Materials Research, 102(1), pp. 6-16. (Year: 2011).*
Karbowniczek, M., J. Gladysz, and W. Ślęzak. "Current situation on the production market of FeMn and FeCr." Journal of Achievements in Materials and Manufacturing Engineering 55, No. 2 (2012): 870-875. (Year: 2012).*
Cobb, "Dictionary of Metals", ASM International (2012), pp. 224.

* cited by examiner

*Primary Examiner* — Jophy S. Koshy
(74) *Attorney, Agent, or Firm* — Carol A. Marmo; Eckert Seamans Cherin & Mellott, LLC

(57) ABSTRACT

The invention relates to biodegradable iron alloy-containing compositions for use in preparing medical devices. In addition, biodegradable crystalline and amorphous compositions of the invention exhibit properties that make them suitable for use as medical devices for implantation into a body of a patient. The compositions include elemental iron and one or more elements selected from manganese, magnesium, zirconium, zinc and calcium. The compositions can be prepared using a high energy milling technique. The resulting compositions and the devices formed therefrom are useful in various surgical procedures, such as but not limited to orthopedic, craniofacial and cardiovascular.

5 Claims, No Drawings

BIODEGRADABLE IRON-CONTAINING COMPOSITIONS, METHODS OF PREPARING AND APPLICATIONS THEREFOR

CROSS REFERENCE TO RELATED APPLICATIONS

This divisional application claims priority under 35 U.S.C. § 119(e) to U.S. patent application Ser. No. 14/045,011, filed Oct. 3, 2013, entitled "BIODEGRADABLE IRON-CONTAINING COMPOSITIONS, METHODS OF PREPARING AND APPLICATIONS THEREFOR", which claims priority to U.S. Provisional Patent Application Ser. No. 61/710,338, filed Oct. 5, 2012, entitled "BIODEGRADABLE IRON-CONTAINING COMPOSITIONS, METHODS OF PREPARING AND APPLICATIONS THEREFOR".

GOVERNMENT SUPPORT

The invention was made with government support under EEC-0812348 awarded by the National Science Foundation. The government has certain rights in the invention.

FIELD OF THE INVENTION

The invention relates to metal alloy-containing compositions and articles, and methods of their preparation. The invention is particularly suitable for use in fabricating biodegradable materials and medical devices for implantation into a patient body, such as for example, orthopedic, craniofacial and cardiovascular implant devices.

BACKGROUND OF THE INVENTION

Metallic implant devices, such as plates, screws, nails and pins are commonly used in the practice of orthopedic and craniofacial implant surgery, and metallic stents are also implanted into a patient body to support lumens, for example, coronary arteries. These metallic implant devices are typically constructed of stainless steel, platinum or titanium. An advantage of these materials of construction is that they exhibit good biomechanical properties. However, a disadvantage is that implant devices constructed of these materials do not degrade over a period of time. Thus, the patient may require surgery to remove the implant device when there is no longer a medical need for the device in the patient. For example, in certain instances, such as pediatric applications, there may be a concern that if an implant device remains in the patient's body after it is determined that there is no longer a need for it, the device may eventually be rejected by the body and cause complications for the patient. Thus, there is room for improvement in medical implant devices and, particularly, in the materials for construction of these devices. For example, it would be advantageous for: (i) the implant device to be constructed of material that is capable of degrading over a period of time, (ii) the implant device to dissolve in a physiological environment such that it would not remain in the body when there is no longer a medical need for it, and (iii) a patient not to be subjected to surgery in order to remove the implant device from its body.

Conventional biomaterials used for orthopedic and craniofacial applications are primarily chosen based on their ability to withstand cyclic load-bearing. Metallic biomaterials, in particular, typically exhibit properties such as high strength, ductility, fracture toughness, hardness, corrosion resistance, formability, and biocompatibility to make them attractive for most load bearing applications. The most prevalent metals known for load-bearing applications are stainless steels, titanium (Ti), and cobalt-chromium (Co—Cr) based alloys, although their stiffness, rigidity, and strength far exceed those of natural bone. Further, their elastic modulus differs significantly from natural bone causing stress-shielding effects that may lead to reduced loading of bone and this decrease in stimulation may result in insufficient new bone growth and less implant stability. With conventional metallic biomaterials there is also a potential risk of toxic metallic ions and particles being released into the patient's body at the implant site through corrosion or wear which may cause an immune response. Implant devices constructed of conventional metallic biomaterials may also lead to hypersensitivity, growth restriction (most significantly for pediatric implants), implant migration, and imaging interference. Due to these complications, it is estimated that 10% of patients having implants may require surgery to remove or replace the implants, e.g., metallic plates and screws, exposing these patients to additional risks, and increasing surgical time and resources.

There is a need and desire to design and develop new load-bearing biomaterials with the objectives of providing adequate support while the natural bone is healing and allowing the implant device to harmlessly degrade over time in the patient's body when the implant device is no longer needed to perform its function in the body.

As a result of this need, degradable biomaterials have recently been developed employing resorbable polymers. However, resorbable polymer fixation plates and screws have been shown to be relatively weaker and less rigid as compared to conventional metallic biomaterials, and have demonstrated local inflammatory reactions. Biodegradable materials which are used as replacements for conventional metallic biomaterials in the construction of implant devices include polymers, such as polyhydroxy acids, polylactic acid (PLA), polyglycolic acid (PGA), and the like. These materials have been found to exhibit relatively poor strength and ductility, and have a tendency to react with human tissue which can limit bone growth.

To overcome the disadvantages associated with resorbable polymer, iron (Fe)-based alloys have emerged as new biodegradable materials for cardiovascular and orthopedic applications. Iron-based alloys have been found to degrade without producing harmful hydrogen gas. The evolution of hydrogen, such as, hydrogen bubbles may result in complications within a body of a patient. Further, iron-based alloys have been found to possess better mechanical properties, e.g., high strength, than degradable magnesium-based alloys. For example, iron has been investigated as a biodegradable stent and showed no significant obstruction of the stented vessel. However, iron is known to degrade very slowly. Further, the various known biodegradable iron-based alloys can exhibit low biocompatibility and/or low corrosion rates, which render these materials unsuitable for use as implant devices.

In the field of biomedical applications, there is a desire to develop improved biodegradable metal alloy-containing implant materials having good compressive strength, corrosion rate matching time of healing of the surrounding tissue, and biocompatibility.

SUMMARY OF THE INVENTION

In one aspect, the invention provides a biodegradable, metal alloy-containing composition including elemental iron and one or more elements selected from the group consisting of manganese, magnesium, zinc, zirconium and calcium.

In certain embodiments, the one or more elements are manganese, magnesium and calcium. In other embodiments, the one or more elements are magnesium, zirconium and calcium, or alternatively, magnesium, zinc and calcium.

The elemental iron may be present in an amount such that it constitutes from about 10.0 weight percent to about 95.0 weight percent based on total weight of the composition. The manganese, magnesium and calcium may be each present in an amount such that the manganese constitutes from about 5.0 weight percent to about 75.0 weight percent, the magnesium constitutes from greater than zero weight percent to about 10.0 weight percent, and the calcium constitutes from greater than zero weight percent to about 10.0 weight percent, based on total weight of the composition. The magnesium, zirconium and calcium may be each present in an amount such that the magnesium constitutes from greater than zero weight percent to about 7.0 weight percent, the zirconium constitutes from about 8.0 weight percent to about 52.0 weight percent, and the calcium constitutes from greater than zero weight percent to about 30.0 weight percent, based on total weight of the composition. The magnesium, zinc and calcium may be each present in an amount such that the magnesium constitutes from greater than zero weight percent to about 10.0 weight percent, the zinc constitutes from greater than zero weight percent to about 10.0 weight percent, and the calcium constitutes from greater than zero weight percent to about 30.0 weight percent, based on total weight of the composition.

In another aspect, the invention provides a method of preparing a biodegradable, metal alloy-containing composition. The method includes charging in a high energy mill elemental iron and one or more elements selected from the group consisting of manganese, magnesium, zirconium, zinc and calcium; and conducting high energy milling of the elemental iron and one or more elements.

The high energy milling may be conducted in dry conditions followed by high energy milling conducted in wet conditions. The material resulting from the high energy milling may be subjected to a casting process to form an iron alloy-containing cast. The iron alloy-containing cast may be finished to produce a biomedical device. The biomedical device may be implanted into a body of a patient. The biomedical device may dissolve in the body of the patient.

DETAILED DESCRIPTION OF THE PREFERRED EMBODIMENTS

This invention relates to novel, biodegradable metal alloy-containing compositions. Further, this invention relates to articles, such as medical devices, which are constructed or fabricated from the biodegradable metal alloy-containing compositions of this invention. Moreover, this invention relates to methods of preparing these biodegradable, metal alloy-containing compositions and articles for use in medical applications, such as but not limited to, orthopedic and craniofacial surgery.

The biodegradable metal alloy-containing compositions include iron (Fe). These Fe-containing compositions also include one or more of the following elements: zirconium (Zr), manganese (Mn), calcium (Ca), magnesium (Mg), and zinc (Zn).

The compositions of the invention can be used as materials of construction to prepare various articles, such as biomedical devices for implantation into a body of a patient for orthopedic, cardiovascular and craniofacial applications.

In addition to the desirable biodegradability property of the metal alloy-containing compositions of the invention, these compositions include at least one of the following characteristics: biocompatibility, corrosion resistance, cell attachment, cell viability and mechanical strength, which make them suitable for use as implant devices in a body of a patient.

The biodegradable metal alloy-containing compositions of the invention include the presence of iron and other elements or compounds in various amounts. In certain embodiments, the other elements can include one or more of zinc (Zn), zirconium (Zr), calcium (Ca), manganese (Mn) and magnesium (Mg). The amount of each of these elements in the compositions can vary. As previously indicated, in general, the amounts of each of these components are selected such that the resulting compositions exhibit one or more of the desired characteristics identified herein, e.g., acceptable non-toxic limits and degradability over an acceptable period of time. For example, the amount of iron is selected such that the compositions exhibit corrosion resistance in the presence of water and simulated biological fluids which allow the compositions to be suitable for in vivo use, for example, in a physiological environment, such as a body of a patient.

The compositions of the invention are capable of controlling the corrosion rate and improving mechanical properties of iron-containing alloys through the introduction of alloying elements and processing conditions. In certain embodiments, the corrosion rate matches or corresponds to the time of healing of surrounding tissue. For example, an implantation device fabricated of the biodegradable metal alloy-containing compositions of the invention degrades or dissolves completely at or near the time it takes for the tissue surrounding the device to heal. Thus, the implantation device is not present for a prolonged period of time, e.g., a time beyond which there is a need for the device. Without intending to be bound by any particular theory, it is believed that corrosion and mechanical properties are strongly affected by alloying elements with iron in a solid solution.

In certain embodiments, the compositions in accordance with the invention include a mixture of one or more elements, such as, Fe, Mn, Mg and Ca. In other embodiments, the compositions include a mixture Fe, Zr, Mg and Ca. In still other embodiments, the compositions include Fe, Zn, Mg and Ca. The amount of each of these elements employed can vary and in general, the amount of each of these elements is selected in order that the resulting compositions are within acceptable non-toxic limits such that the compositions are sufficiently biocompatible for implantation into a body of a patient, and are degradable over a period of time so that the implantation device does not remain in the body of the patient for prolonged periods of time, e.g., beyond the period of time when there is a medical need for the implantation device.

The elemental iron may be present in an amount such that it constitutes from about 10.0 weight percent to about 95.0 weight percent based on total weight of the composition. The manganese, magnesium and calcium may be each present in an amount such that the manganese constitutes from about 5.0 weight percent to about 75.0 weight percent, the magnesium constitutes from greater than zero weight percent to about 10.0 weight percent, and the calcium constitutes from greater than zero weight percent to about 10.0 weight percent, based on total weight of the composition. The magnesium, zirconium and calcium may be each present in an amount such that the magnesium constitutes from greater than zero weight percent to about 7.0 weight percent, the zirconium constitutes from about 8.0 weight percent to about 52.0 weight percent, and the calcium constitutes from greater than zero weight percent to about 30.0 weight percent, based on total weight of the composition. The magnesium, zinc and calcium may be each present in an amount such that the magnesium constitutes from greater than zero weight percent to about 10.0 weight percent, the zinc constitutes from greater than zero weight percent to about 10.0 weight percent, and the calcium constitutes from greater than zero weight percent to about 30.0 weight percent, based on total weight of the composition.

An implantation device fabricated in accordance with the invention will degrade and preferably dissolve completely within an acceptable time frame. For example, an implant device fabricated of a composition in accordance with the invention can serve as filler or support material during a natural bone healing process and following completion of this process, the implant device will degrade within an acceptable time period and therefore, will not remain in the body for a prolonged period of time. Suitable non-toxic limits and an acceptable time frame for degradation can vary and may depend on the physical and physiological characteristics of the patient, the in vitro site of the implantation device, and the medical use of the implantation device. Without intending to be bound by any particular theory, it is believed that the presence of iron contributes to the improved mechanical strength and controlled corrosion of the biodegradable compositions.

Non-limiting examples of medical devices in which the compositions and articles of the invention can be used include, but are not limited to, plates, meshes, staples, screws, pins, tacks, rods, suture anchors, tubular mesh, coils, X-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, nerve guides, surgical implants and wires. In a preferred embodiment, the medical devices include fixation bone plates and screws, temporo-mandibular joints, cardiovascular stents, and nerve guides.

In certain embodiments, the medical implant devices described herein can have at least one active substance attached thereto. The active substance can be attached to the surface of the device or encapsulated within the device. As used herein, the term "active substance" refers to a molecule, compound, complex, adduct and/or composite that exhibits one or more beneficial activities such as therapeutic activity, diagnostic activity, biocompatibility, corrosion-resistance, and the like. Active substances that exhibit a therapeutic activity can include bioactive agents, pharmaceutically active agents, drugs and the like. Non-limiting examples of bioactive agents that can be incorporated in the compositions, articles and devices of the invention include, but are not limited to, bone growth promoting agents such as growth factors, drugs, proteins, antibiotics, antibodies, ligands, DNA, RNA, peptides, enzymes, vitamins, cells and the like, and combinations thereof.

It is contemplated that additional components may be added to the biodegradable, metal alloy-containing compositions of the invention provided that the non-toxicity and biodegradability of the compositions is maintained within acceptable limits. The additional components can be selected from a wide variety known in the art and can include but are not limited to strontium, silver and mixtures thereof.

In certain embodiments, the compositions of the invention do not include zinc. In certain other embodiments, the compositions of the invention include the presence of zinc in amounts that maintain the toxicity levels of the compositions within acceptable limits. It is known generally in the art that the presence of zinc in particular amounts, i.e., an unacceptable level, can produce an undesirable or unacceptable level of toxicity in a physiological environment, such as a body of a patient.

The biodegradable, metal alloy-containing compositions of the invention can be prepared using various methods and processes. In general, powder metallurgy methods and processes are employed.

For example, melting and casting processes may be employed. It is known in the art of metallurgy that casting is a production technique in which a metal or a mixture of metals is heated until it is molten and then, it is poured into a mold, allowed to cool and solidify. In one embodiment, the iron and other selected elements are melted by heating at an elevated temperature, preferably under a protective atmosphere, and then poured into a mold, allowed to cool and solidify.

Casting of the composition can be affected by using any casting procedure known in the art, such as, but not limited to, sand casting, gravity casting, direct chill casting, centrifugal casting, die casting, plaster casting and investment casting. It is believed that the particular process used for casting can affect the properties and characteristics of the cast composition. Further, it is believed that the temperature at which the melting procedure is performed can also affect the composition. Thus, the temperature may be carefully selected so as to maintain the desired composition of the alloy.

In one embodiment, prior to solidification, the molten mixture is tested to determine the amount of the various components therein and therefore, to provide an opportunity to adjust the amounts as desired prior to solidification.

In another embodiment, the melting and/or casting steps are/is performed under a protective atmosphere to preclude, minimize or reduce the components of the composition from decomposing/oxidation. In particular, it is desired to preclude, minimize or reduce the decomposition/oxidation of magnesium in the composition. The protective atmosphere can include compounds selected from those known in the art, such as but not limited to, argon, sulfur hexafluoride and mixtures thereof.

In yet another embodiment, subsequent to the casting process, the iron alloy-containing cast is subjected to homogenization. Without intending to be bound by any particular theory, it is believed that a homogenization treatment can cause the dissolution of impurities and intermetallic phases.

In further embodiments, the obtained cast can be subjected to various forming and finishing processes known in the art. Non-limiting examples of such processes include, but are not limited to, extrusion, forging, rolling, polishing (by mechanical and/or chemical means), surface treating (to form a superficial layer on the surface) and combinations thereof.

The resulting cast can be formed, finished, machined and manipulated to produce articles and devices for use in medical applications, such as medical devices for implantation into a body of a patient. Furthermore, these medical devices can be used in orthopedic, craniofacial and cardiovascular applications.

In certain embodiments of the invention, Fe and one or more of Mn, Mg, Ca, Zr and Zn are alloyed by employing high energy mechanical alloying (HEMA) and uniaxial or isostatic compaction and sintering. The compositions used for HEMA can include, but are not limited to, the following: (i) Fe, Mn, Mg and Ca or (ii) Fe, Zr, Mg and Ca or (iii) Fe, Zn, Mg and Ca. For example, the Fe and other selected elements in powder form are charged to a high energy mechanical mill. Further, stainless steel (SS) balls are included in the charge with the elements. The SS balls typically used in a HEMA process have a diameter in the range of from 5 mm to 8 mm. The amount of each of the charge components can vary. In alternate embodiments, the charge ratio of the balls to the elements (e.g., powder) can be 20:1 or 10:1 or 8:1 or 5:1. Different charge ratios can cause variations in the kinetics of the milling. Further, the duration of the milling also can vary depending on the amount of time needed to produce a homogeneous mixture. In certain embodiments, the milling can be conducted for up to 15 or 20 hours. Upon completion of the milling, a homogeneous alloy mixture is formed.

The milling can be conducted in dry or wet conditions. In wet conditions, suitable inert solvents can be selected from the wide variety known in the art, such as, for example, but not limited to, toluene, xylene, N-methyl-2-pyrrolidone (NMP), acetonitrile and mixtures thereof. In certain embodiments, the elements are milled in dry conditions followed by milling in wet conditions.

The HEMA may be performed under a protective atmosphere to preclude, minimize, or reduce decomposition of the elements in the compositions. In particular, it is desirable to preclude, minimize, or reduce the decomposition of magnesium in the compositions. Magnesium is known to be a non-toxic metal element that degrades in a physiological environment and therefore, is considered a suitable element for use in constructing biodegradable implant devices. However, disadvantageously, the degradation of magnesium in a physiological environment yields magnesium hydroxide and hydrogen gas. This process is known in the art as magnesium corrosion. The hydrogen gas produced in the body of the patient as a result of magnesium corrosion can produce complications because the ability of the human body to absorb or release hydrogen gas is limited.

As above-mentioned, the protective atmosphere can include compounds selected from those known in the art, such as but not limited to, argon, sulfur hexafluoride and mixtures thereof.

In certain embodiments, subsequent to HEMA, amorphous metal films are synthesized by pulsed laser deposition (PLD).

Detailed exemplary procedures for performing the melting and casting processes are depicted in the examples herein.

Additional objects, advantages and features of the invention may become apparent to one of ordinary skill in the art based on the following examples, which are provided for illustrative purposes and are not intended to be limiting.

EXAMPLES

Example 1

Fe—Mn System by HEMA, Compaction and Sintering
Experimental Method
1.1 Synthesis of Sintering the Compacted Fe—Mn Based Crystalline Powder by High Energy Mechanical Alloying (HEMA)

All alloys were produced by high energy mechanical alloying (HEMA) and compaction. Elemental powders of pure elemental Fe, Mn, Mg, and Ca were commercially obtained and loaded into stainless steel vials containing 5 mm diameter stainless steel balls inside an argon-filled glove box in which the oxygen concentration was kept below 1.0 ppm. The weight of the starting mixture was approximately 60 g and the total ball weight was approximately 600 g (ball to powder ratio was 10:1). The mixture was subjected to dry milling in a planetary Fritsch P5 high energy Shaker Mill for up to 20 hours with 30 minute resting intervals after every one hour of milling. Post dry milling, 15 ml of toluene (anhydrous, 99.8%, Sigma-Aldrich) was loaded in the vial and the mixture was subsequently wet milled for a period of up to 8 hours to reduce the adhesion of powders on the balls and the inner surface of the milling vial. The post ball milled powders were dried and then compacted at a pressure of 2500 psi and 60 ksi using a Carver Press 4350 and Flow Autoclave System cold isostatic compaction press to produce 10 and 25.0 mm diameter discs to be sintered at a temperature of 1200° C. for 3 hours.
1.2 MTT Cell Viability Assay MTT (3-(4,5-Dimethylthiazol-2-yl)-2,5-diphenyltetrazolium bromide) assay was used to assess the cytotoxicity of degradation product after 72 h immersion of specimens in culture medium. Dulbecco's modified eagle medium (α-MEM) with 10% fetal bovine serum (FBS) was used. Extract media diluted to 50%, 25%, and 10%, as well as 100% extract media were added to the 24 h cultured MC3T3 cell and, MTT assay was performed after 24 h and 72 h culture. Before adding MTT formazan salt to wells, the extract medium was replaced with a regular cell culture medium.
1.3 Electrochemical Corrosion Measurement A three-electrode setup (Ag/AgCl reference electrode, platinum wire being counter electrode) was used to measure the electrochemical corrosion properties in Dulbecco's modified eagle medium (DMEM) supplemented with 10% fetal bovine serum (FBS) and 1% penicillin/streptomycin (P/S). Potentiodynamic polarization scans were performed after 15 min of immersion between −1 and −2 V at a scan rate of 1 mVs$^{-1}$ using a CH instrument potentiostat (CHI 604A) at ~37.4° C. Corrosion current ($i_{corr}$) and potential ($E_{corr}$) were calculated from extrapolated data of the cathodic and anodic part of a tafel plot.
1.4 Summarized Results
Anticipated Systems A Fe-35Mn system is a potential composition of Fe-based degradable metallic biomaterials suitable for fabricating implant devices with a longer degradation time as compared to Mg-based devices. With the knowledge that different elements at different weight ratios can enhance the degradation, magnesium and calcium were evaluated to show that addition of these elements can serve to control the corrosion characteristics.

The substitution of 1-10% Mn for Mg or Ca exhibited an increase in the corrosion rate obtained by potentiodynamic polarization measurement. In both Fe—Mn—Mg and Fe—

Mn—Ca, the corrosion potential increased towards more positive potential and the current density also increased, suggesting an increase in corrosion rate. Fe—Mn—Ca showed acceptable cell viability during 1 and 3 day MTT assay.

Fe-5-40% Mn—X and Fe-5-40% Mn—X—Y systems were processed where X and Y were trace elements to control the corrosion behavior with amounts below toxic thresholds. Potential elements for X and Y included known biocompatible elements such as Mg, Zn, Al, Y, Zr, Ti, Ta, Ca, Sr, and Ce in amounts greater than zero and not higher than 10%. These powder alloys were processed using HEMA, compaction, and sintering, or through additive manufacturing methods such as 3D printing or selective laser melting.

The results in Table 1 show the corrosion potential, current density and corrosion rate for Fe—Mn, Fe—Mn—Ca, Fe—Mn—Mg and pure Mg compositions, and as-extruded AZ31 from potentiodynamic polarization measurement.

TABLE 1

| Materials | Corrosion Potential $E_{corr}$ (V) | Corrosion Current Density $i_{corr}$ (μA cm$^{-2}$) | Corrosion Rate (mm/year) |
| --- | --- | --- | --- |
| Pure Mg | −1.57 | 35.19 | 0.80 |
| AZ 31 | −1.48 | 19.20 | 0.43 |
| Fe—35Mn | −0.65 | −6.97 | 0.05 |
| Fe—30Mn—5Ca | −0.56 | −19.02 | 0.18 |
| Fe—30Mn—5Mg | −0.60 | −11.20 | 0.11 |

Example 2

Fe—Zr—Ca, Fe—Zr—Mg, Fe—Zr—Ca—Mg System by HEMA, PLD
Experimental Method
2.1. Synthesis of Amorphous/Crystalline Powder by High Energy Mechanical Alloying (HEMA)

All alloys were produced by high energy mechanical alloying (HEMA) and compaction. Commercial elemental powders of pure Fe (99.9+%, <10 μm, Alfa Aesar), pure Zr (99.6%, -325 mesh, Alfa Aesar), pure Mg (99.8%, <325 mesh, Alfa Aesar), Zn (97.5%, 6-9 μm, Alfa Aesar) and Ca (99.5%, <16 mesh, Alfa Aesar) were chosen as the starting materials. For Fe—Zr—Ca systems, each composition was accurately weighed including from about 0.6 weight percent to about 29.8 weight percent of calcium, from about 13.9 weight percent to about 52 weight percent of zirconium, and a balance of iron, based on the total weight of the composition. An amorphous structure was formed above 60 weight percent of iron in the Fe—Zr—Ca system. The Fe—Zr—Mg system included from about 0.4 weight percent to about 6.9 weight percent of magnesium, from about 8.6 weight percent to about 27.8 weight percent of zirconium, and a balance of iron, based on the total weight of the composition. In Fe—Zr—Ca—Mg system, each composition was accurately weighed including from greater than zero to about 0.8 weight percent of magnesium, from about 0.6 weight percent to about 0.7 weight percent of calcium, from about 27.8 weight percent to about 28.1 weight percent of zirconium, and a balance of iron, based on the total weight of the composition. For Fe—Zn—X system and Fe—Zn—X—Y system, each composition was accurately weighed including from about 1 weight percent to about 10 weight percent of X and Y, from about 30 weight percent to about 50 weight percent of zinc, and a balance of iron, based on the total weight of the composition. Potential elements for X and Y elements were Ca, Mg, Y, Ti, Ta, Sr, and Ce as biocompatible elements. For Mg—Zn—Fe—Zr—Ca system, it was weighed including from about 1 weight percent to about 10 weight percent of iron, zirconium and calcium, from about 30 weight percent to about 50 weight percent of zinc, and a balance of magnesium, based on the total weight of the composition. For Mg—Zr—Ca system, it was weighed including from about 1 weight percent to about 10 weight percent of calcium, from about 30 weight percent to about 65 weight percent of zirconium, and a balance of magnesium, based on the total weight of the composition. The mixture of elemental powder was loaded into stainless steel (SS) vials containing 2 mm diameter SS balls as the milling media. The ball to powder weight ratio (BPR) was 15 to 1, and the total weight of the starting mixture was 3 g. The mixture was subjected to dry milling in a planetary SPEX 8000 high energy Shaker Mill for up to 10 hours with 30 minute resting intervals after every one hour of milling. Post dry milling, 2 ml of toluene (anhydrous, 99.8%, Sigma-Aldrich) was loaded in the vial and the mixture was subsequently wet milled for a period of up to 7 hours to reduce the adhesion of powders on the balls and the inner surface of the milling vial. Handling of the powders and loading of toluene were conducted inside an argon-filled glove box in which the oxygen concentration was kept below 1.0 ppm. The post ball milled powders were dried and then compacted at a pressure of 60 psi using Flow Autoclave System cold isostatic compaction press to produce 25.0 mm diameter discs to be used as targets for PLD (Pulsed Laser Deposition).

2.2. Synthesis of Amorphous/Crystalline Metal Coating Layer by Pulsed Laser Deposition (PLD)

All thin films were produced by PLD utilizing a 248 nm KrF excimer laser irradiation pulsed at 25 ns FWHM in a high vacuum chamber with a base pressure of $10^{-6}$ Torr. In all depositions the spot size was approximately 1×3 mm, the fluence 8.3-9.6 J/cm$^2$, the laser pulse frequency of 10 Hz and the deposition rate about 2.3 Å/s. The target to substrate distance was maintained constant at 58 mm, with targets rotated during deposition. Films were deposited at room temperature for a deposition time of 30 minutes on amorphous SiO$_2$ glass for glancing angle XRD and the cytocompatibility tests.

2.3. Cytocompatibility

Cell biocompatibility of the alloy system was evaluated for Fe—Zr—Ca, Fe—Zr—Mg and Fe—Zr—Ca—Mg systems. Each alloy system was deposited on amorphous glass by PLD and then cell viability tests were conducted. Murine MC3T3-E1 pre-osteoblast cells, murine NIH3T3 fibroblast cells, and human mesenchymal stem cells were utilized for cell culture studies. These three kinds of cell lines were cultured on deposited film of each alloy system on glass for 24 or 72 hours and assessed using the Live/Dead cell viability assay. Cells were observed and imaged using fluorescent microscopy.

2.4. Characterization Method

The microstructure and phase assemblage of thin films and milled powders were examined by glancing angle (Philips PW 1830 with Cu-Kα radiation) and conventional X-ray diffraction (PANalytical X'pert Pro with Cu-Ku radiation). A JEOL JEM2000FX operating at 200 kV was used for conducting transmission electron microscopy (TEM) and obtaining conventional bright field images. TEM samples were obtained by directly depositing the film by PLD on silicon nitride supported window grids (Ted Pella, USA) for observation under the TEM. Additionally, samples were made by depositing the films on oxidized silicon wafer containing a photo-resist following the above method. Films were lifted off from the substrate by stripping the photo-resist and transferring onto standard TEM copper membrane grid (Ted Pella, USA) for observation under the TEM.

The results are shown in Tables 2, 3, 4 and 5.

3.0 SUMMARIZED RESULTS

The cytocompatibility tests showed reasonable biocompatibility after 24 and 72 hours cell culture using the Live/Dead cell viability assay for each deposited thin films of Fe—Zr—Ca, Fe—Zr—Mg and Fe—Zr—Ca—Mg systems. These as-milled powder and deposited films have amorphous structure as confirmed by XRD and TEM. These results indicate the feasibility of generating biocompatible amorphous Fe-based alloy coatings.

TABLE 2

Fe—Zr—Ca System

| Composition | Structure |
| --- | --- |
| $Fe_{71}Zr_{29}$ | amorphous |
| $Fe_{71.6}Zr_{27.8}Ca_{0.6}$ | amorphous |
| $Fe_{72.2}Zr_{26.5}Ca_{1.3}$ | Close to amorphous |
| $Fe_{70.9}Zr_{27.8}Ca_{1.3}$ | Close to amorphous |
| $Fe_{72.8}Zr_{25.2}Ca_{2}$ | Close to amorphous |
| $Fe_{74}Zr_{22.7}Ca_{3.3}$ | Close to amorphous |
| $Fe_{75.3}Zr_{20}Ca_{4.7}$ | Close to amorphous |
| $Fe_{77.3}Zr_{15.8}Ca_{6.9}$ | amorphous |
| $Fe_{63.7}Zr_{29.8}Ca_{6.5}$ | amorphous |
| $Fe_{43.3}Zr_{52}Ca_{4.7}$ | crystalline |
| $Fe_{56.3}Ca_{29.8}Zr_{13.9}$ | crystalline |

TABLE 3

Fe—Zr—Mg System

| Composition | Structure |
| --- | --- |
| $Fe_{71.8}Zr_{27.8}Mg_{0.4}$* | amorphous |
| $Fe_{72.5}Zr_{26.7}Mg_{0.8}$* | amorphous |
| $Fe_{73.3}Zr_{25.5}Mg_{1.2}$* | amorphous |
| $Fe_{74.2}Zr_{24.2}Mg_{1.6}$* | amorphous |
| $Fe_{71.5}Zr_{26.9}Mg_{1.6}$* | Close to amorphous |
| $Fe_{72.8}Zr_{25.6}Mg_{1.6}$* | Close to amorphous |
| $Fe_{79.5}Zr_{16.2}Mg_{4.3}$* | amorphous |
| $Fe_{84.5}Zr_{8.6}Mg_{6.9}$* | amorphous |

*The Mg in the Fe—Zr—Mg system above can include Mg-containing alloys.

TABLE 4

Fe—Zr—Ca—Mg System

| Composition | Structure |
| --- | --- |
| $Fe_{71.53}Zr_{27.79}Ca_{0.64}Mg_{0.04}$ | amorphous |
| $Fe_{71.32}Zr_{27.84}Ca_{0.64}Mg_{0.2}$ | amorphous |
| $Fe_{71.21}Zr_{27.87}Ca_{0.64}Mg_{0.28}$ | amorphous |
| $Fe_{71.05}Zr_{27.91}Ca_{0.65}Mg_{0.39}$ | amorphous |
| $Fe_{70.78}Zr_{27.98}Ca_{0.65}Mg_{0.59}$ | amorphous |
| $Fe_{70.5}Zr_{28.06}Ca_{0.65}Mg_{0.79}$ | amorphous |

TABLE 5

Other Systems

| Composition | Structure |
| --- | --- |
| $Fe_{50.8}Zn_{43.7}Ca_{5.5}$ | amorphous |
| $Fe_{58.1}Zn_{36.3}Ca_{5.6}$ | amorphous |
| $Fe_{51.9}Zn_{44.7}Mg_{3.4}$ | Close to amorphous |
| $Mg_{30.1}Zr_{65.8}Ca_{4.1}$ | Crystalline |
| $Mg_{37.1}Zn_{46.6}Fe_{8}Zr_{3.2}Ca_{5.1}$ | Close to amorphous |
| $Fe_{53.2}Zn_{38.1}Mg_{2.9}Ca_{5.8}$ | Close to amorphous |

4.0 Fe—Mg—Zn, Fe—Ca—Zn, Fe—Mn—Mg—Zn, and Fe—Mn—Ca—Zn ALLOYS COMPUTATIONAL STUDY It is generally known that pure Fe corrodes much slower in aqueous environments than Mg and its alloys. Fe-based alloys with improved dissolution kinetics, enabling them to degrade faster, would allow for the manufacture of materials having controlled degradation. Addition of an appreciable amount of suitable alloying elements with lower electrochemical potential in comparison to Mg was evaluated to increase the degradation rate to level suitable for bio-applications. It was evaluated whether galvanic corrosion between the different phases of the compound played a positive role in accelerating the much desirable biodegradation.

Fe-based ternary compositions were prepared according to the following compositions (weight %):

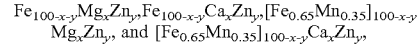

wherein 55≤x≤65, 12≤y≤70 and x+y<100.

A thermodynamic evaluation of the hydrolytic reactions was conducted:

$$Fe—Mg—Zn+2H_2O => [Fe—Mg—Zn](OH)_2+H_2\uparrow \quad (1)$$

$$Fe—Ca—Zn+2H_2O => [Fe—Ca—Zn](OH)_2+H_2\uparrow \quad (2)$$

$$Fe—Mn—Mg—Zn+2H_2O => [Fe—Mg—Mn—Zn](OH)_2+H_2\uparrow \quad (3)$$

$$Fe—Mn—Ca—Zn+2H_2O => [Fe—Mn—Ca—Zn](OH)_2+H_2\uparrow \quad (4)$$

A comparison was made of the heat of the reaction $\Delta G^0$ with those calculated for hydrolysis of pure Fe and Mg:

$$Fe+2H_2O => Fe(OH)_2+H_2\uparrow \quad (5)$$

$$Mg+2H_2O => Mg(OH)_2+H_2\uparrow \quad (6)$$

Results were obtained from the thermodynamic calculations using a CALPHAD approach. The results showed that the more negative was the free energy change, the higher thermodynamic stimulus of the hydrolytic reaction was observed in comparison with pure Fe for which $\delta\Delta G^0=0$. For pure Mg $\delta\Delta G^0=-361$ kJ/mol there was indicated an increased propensity of Mg to react with water in comparison with Fe. The region between $\delta\Delta G^0=0$ and −361 kJ/mol reflected alloys with intermediate stimulus for the reaction, which may be useful for designing alloys with controlled degradation since the corrosion rate may be directly dependent on the composition of the alloy.

5.0 RESULTS

Fe-(4.4-36.6) wt. % Mg-(35.5-49.3) wt % Zn and Fe-(4.3-27.7) wt. % Mg-(46.3-59.6) wt. % Zn were synthesized by high energy mechanical alloying (HEMA) using elemental blends of iron (Alfa Aesar 99.9%), zinc (Alfa Aesar>99.95%), and magnesium (Alfa Aesar 99.9%) powders which were mechanically milled in a high energy shaker mill (SPEX CeriPrep 8000M) for 10 h in a stainless steel (SS) vial using 20 SS balls of 2 mm diameter (~20 g) with a ball to powder weight ratio of 10:1. To determine the phase formation in the mechanically milled powder, X-ray diffraction (XRD) was carried out using Philips PW1830 system employing the $CuK_\alpha$ ($\lambda$=0.15406 nm) radiation.

Powder XRD pattern of $Fe_{49.4}Mg_{4.3}Zn_{46.3}$ and $Fe_{41.9}Mg_{9.1}Zn_{49}$ formed metastable solid solution of Zn (Fe Mg) hcp structures. With an increase of magnesium content ($Fe_{33.4}Mg_{14.5}Zn_{52.1}$, $Fe_{23.7}Mg_{20.7}Zn_{55.6}$) above 9 wt. %, the structure became amorphous which co-existed with metastable Zn (Fe Mg) hcp structure.

XRD pattern of $Fe_{53.3}Mg_{9.3}Zn_{37.4}$ and $Fe_{60.3}Mg_{4.4}Zn_{35.3}$ formed amorphous phase which co-exist with metastable Zn(Fe Mg) hcp structure. However, with increase of magnesium content ($Fe_{36.3}Mg_{21.1}Zn_{42.6}$, $Fe_{45.4}Mg_{14.8}Zn_{39.8}$) above 9 wt. % metastable solid solution of Zn (Fe Mg) hcp structure was observed.

The Mg in the Fe—Zn—Mg system above may include Mg-containing alloys.

The above also was applied to Fe-based ternary compositions with following compositions (weight %):

$$Fe_{100-x-y}Ca_xZn_y$$

wherein 5≤x≤65, 12≤y≤70 and x+y<100.

6.0 CONCLUSION

The results indicated that the metal alloy-containing compositions in accordance with the invention exhibited excellent corrosion behavior. Further, cellular attachment and live/dead assays showed very good attachment of cells, which was superior to controls tested. Thus, the metal alloy-containing compositions in accordance with the invention are deemed suitable for use in fabricating medical implantation devices for applications where controlled degradation and excellent cell compatibility are desired.

The invention claimed is:

1. A biodegradable iron-based metal alloy, consisting of:
 from 0.04 to 0.79 weight percent magnesium;
 from 27.79 to 27.98 weight percent zirconium;
 from 0.64 to 0.65 weight percent calcium; and
 a remainder of iron,
 wherein the metal alloy is biodegradable and structurally amorphous.

2. A biodegradable medical device comprising the iron-based alloy of claim 1.

3. The device of claim 2, wherein said device is selected from the group consisting of plate, mesh, staple, screw, pin, tack, rod, suture anchor, tubular mesh, coil, x-ray marker, catheter, pipe, shield, bolt, clip, plug, dental implant, graft device, endoprosthesis, bone-fracture healing device, bone replacement device, joint replacement device, tissue regeneration device, cardiovascular stent, nerve guide, surgical implant, surgical wire and combinations thereof.

4. The device of claim 2, wherein said device is an implantable device.

5. The device of claim 4, wherein the implantable device is selected from the group consisting of an orthopedic device, a craniofacial device and a cardiovascular device.

* * * * *